US012797376B2

(12) United States Patent
Hwang et al.

(10) Patent No.: US 12,797,376 B2
(45) Date of Patent: Nov. 17, 2026

(54) PHARMACEUTICAL COMPOSITION FOR PREVENTION OR TREATMENT OF ALLERGIC SKIN DISEASE OR SKIN PRURITUS

(71) Applicant: CUePEAK BIO. Co., Ltd., Daejeon (KR)

(72) Inventors: Joonsung Hwang, Daejeon (KR); Jeeeune Kim, Seongnam-si (KR)

(73) Assignee: CUePEAK BIO. Co., Ltd., Daejeon (KR)

( * ) Notice: Subject to any disclaimer, the term of this patent is extended or adjusted under 35 U.S.C. 154(b) by 345 days.

(21) Appl. No.: 18/588,090

(22) Filed: Feb. 27, 2024

(65) Prior Publication Data

US 2024/0325358 A1 Oct. 3, 2024

(30) Foreign Application Priority Data

Feb. 27, 2023 (KR) ........................ 10-2023-0025940
Jun. 16, 2023 (KR) ........................ 10-2023-0077188

(51) Int. Cl.

*A61K 31/44* (2006.01)
*A61K 8/49* (2006.01)
*A61K 31/4015* (2006.01)
*A61Q 19/00* (2006.01)

(52) U.S. Cl.

CPC ............ *A61K 31/44* (2013.01); *A61K 8/4913* (2013.01); *A61K 8/4933* (2013.01); *A61K 31/4015* (2013.01); *A61Q 19/00* (2013.01)

(58) Field of Classification Search

CPC ...................................................... A61K 31/44
See application file for complete search history.

(56) References Cited

U.S. PATENT DOCUMENTS 5,401,738 A * 3/1995 Mederski ............. C07D 417/04 544/239
8,673,908 B2 3/2014 Amishiro et al.
8,809,545 B2 8/2014 Chamoin et al.
10,457,637 B2 10/2019 Musicki et al.
2008/0293720 A1 11/2008 Cleary et al.
2011/0237584 A1 9/2011 Amishiro et al.
2013/0296309 A1 11/2013 Chamoin et al.
2018/0170869 A1 6/2018 Musicki et al.
2021/0030716 A1 2/2021 Kim et al.
2022/0151959 A1 5/2022 Kim et al.

FOREIGN PATENT DOCUMENTS

KR 20150043028 A 4/2015
KR 101839391 B1 3/2018
KR 10-2020-0104238 A 9/2020
KR 20210093174 A 7/2021
KR 20220136979 A 10/2022

OTHER PUBLICATIONS

Examination Report of AU 2024229033, mailed Aug. 7, 2026.
Yee, K., W.L., et al. "Phase1 Study of ABT-751, a Novel Microtubule Inhibitor, in Patients with Refractory Hematologic Malignancies" Clin Cancer Res 2005;11(18) Sep. 15, 2005, pp. 6615-6624.
Vanderbilt-Ingram Cancer Centre: "A phase 1/2 trial of ABT-751 in Treating Patients With Metastatic Prostate Cancer That Did Not Respond to Hormone Therapy", Record History | ver. 16: Jun. 27, 2012 | NCT00471718 | ClinicalTrials.gov., pp. 1-28.
Das, L., "A mechanistic study of the binding of TN-16 to tubulin", J. Indian Chem. Soc, vol. 97, No. 11a, Nov. 2020, pp. 2172-2179.
Canela, M., et al., "Novel Colchicine-Site Binders with a Cyclohexanedione Scaffold Identified through a Ligand-Based Virtual Screening Approach", J. Med. Chem. 2014, vol. 57, pp. 3924-3938.

* cited by examiner

*Primary Examiner* — Rei Tsang Shiao
(74) *Attorney, Agent, or Firm* — DICKINSON WRIGHT PLLC

(57) ABSTRACT

Provided is a pharmaceutical composition for preventing or treating allergic skin diseases or pruritus cutaneous, and more particularly, a pharmaceutical composition for preventing or treating allergic skin diseases or pruritus cutaneous including ABT-751 or TN-16 as an effective component, a cosmetic composition for preventing or improving allergic skin diseases or pruritus cutaneous including ABT-751 or TN-16 as an effective component, and a cosmetic composition for skin moisturizing including ABT-751 or TN-16 as an effective component are provided. The composition for preventing, improving, or treating atopic dermatitis according to the present invention was confirmed to effectively increase filaggrin expression in skin cells and improve a skin barrier function, thereby showing an effect of effectively improving or treating symptoms of pruritus cutaneous or allergic skin diseases including atopic dermatitis, and thus, showing an excellent skin moisturizing effect.

12 Claims, 4 Drawing Sheets

PHARMACEUTICAL COMPOSITION FOR PREVENTION OR TREATMENT OF ALLERGIC SKIN DISEASE OR SKIN PRURITUS

CROSS-REFERENCE TO RELATED APPLICATIONS

This application claims priority under 35 U.S.C. § 119 to Korean Patent Applications No. 10-2023-0025940, filed on Feb. 27, 2023, and No. 10-2023-0077188, filed on Jun. 16, 2023, in the Korean Intellectual Property Office, the disclosure of which is incorporated herein by reference in its entirety.

TECHNICAL FIELD

The following disclosure relates to a pharmaceutical composition for preventing or treating allergic skin diseases or pruritus cutaneous, and the like, and more particularly, to a pharmaceutical composition for preventing or treating allergic skin diseases or pruritus cutaneous including ABT-751 or TN-16 as an effective component, a cosmetic composition for preventing or improving allergic skin diseases or pruritus cutaneous including ABT-751 or TN-16 as an effective component, a cosmetic composition for skin moisturizing including ABT-751 or TN-16 as an effective component, and the like.

BACKGROUND

Atopic dermatitis is a chronic and recurrent inflammatory skin disease which mainly begins in infancy or childhood, and has many patients reaching 150 million in 9 global countries including US, UK, and China, and the related therapeutics market is expected to grow to about 8 trillion KRW in 2025.

In Korea, the number of patients receiving treatment for atopic dermatitis each year reaches 1 million, and in particular, since the incidence rate is high in infants and young children, infant and toddler patients aged 0 to 4 years old account for nearly 30% of the total patients and pediatric patients under 9 years of age account for a half of the total patients.

The reason why the prevalence rate of atopic dermatitis is increasing both domestically and internationally is the high incidence rate, but also the absence of a diagnostic method which may accurately diagnose the etiology and an appropriate therapeutic method. Currently, diagnosis of atopic dermatitis is mainly carried out through questionnaires or visual examinations, and steroids or immunosuppressants which are not related to the etiology are used as the therapeutic agent. The immunosuppressant does not have relatively severe side effects, but may not be prescribed for infants and toddlers under 2 years of age who have a particularly high incidence rate, and when the timing of treatment for infants and toddlers in desperate need of early treatment is missed in the early stages of diseases, prolongation and deepening of the diseases are caused.

To date, antibody therapeutics have been developed by global pharmaceutical companies, but they may be prescribed only for severe patients over 12 years of age and may not be used for treating infants and toddlers, and thus, there is an urgent need for a fundamental solution thereto.

SUMMARY

An embodiment of the present invention is directed to providing a pharmaceutical composition for preventing or treating allergic skin diseases or pruritus cutaneous including ABT-751 or TN-16 as an effective component, a cosmetic composition for preventing or improving allergic skin diseases or pruritus cutaneous including ABT-751 or TN-16 as an effective component, and a cosmetic composition for skin moisturizing including ABT-751 or TN-16 as an effective component.

In one general aspect, a pharmaceutical composition for preventing or treating allergic skin diseases or pruritus cutaneous including a compound represented by the following Chemical Formula I or II or a pharmaceutically acceptable salt thereof as an effective component and a method of using the composition are provided:

[Chemical Formula I]

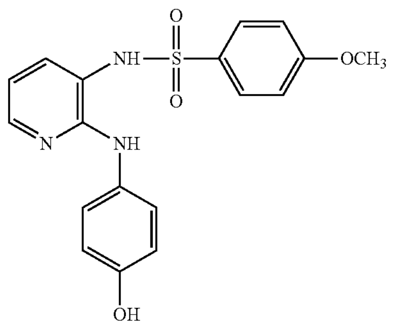

[Chemical Formula II]

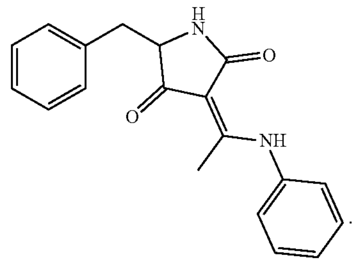

In an exemplary embodiment of the present invention, the allergic skin disease may be atopic dermatitis or contact dermatitis.

In an exemplary embodiment of the present invention, the allergic skin disease may be atopic dermatitis.

In an exemplary embodiment of the present invention, the pharmaceutical composition may be administered by skin application.

In an exemplary embodiment of the present invention, the atopic dermatitis is caused by reduced expression of filaggrin.

In an exemplary embodiment of the present invention, when the reduced expression of filaggrin is 5.0% or more as compared with a normal person, the pharmaceutical composition is administered to a patient.

In an exemplary embodiment of the present invention, the pharmaceutical composition may be any one formulation selected from the group consisting of an ointment agent, a cream agent, a lotion agent, a gel agent, an external solution agent, a paste agent, a liniment agent, and an airol agent.

In another general aspect, a cosmetic composition for preventing or improving allergic skin diseases or pruritus cutaneous including a compound represented by the following Chemical Formula I or II as an effective component and a method of using the composition are provided.

In an exemplary embodiment of the present invention, the cosmetic composition may be any one formulation selected from the group consisting of a solution, an external ointment, a cream, a foam, a nourishing lotion, a softening lotion, a pack, a softener, a milky lotion, a makeup base, an essence, a soap, a liquid detergent, a bath preparation, a sunscreen cream, a sun oil, a suspension, an emulsion, a paste, a gel, a lotion, a powder, a soap, a surfactant-containing cleanser, an oil, a powder foundation, an emulsion foundation, a wax foundation, a patch, and a spray.

In another general aspect, a cosmetic composition for skin moisturizing including a compound represented by the following Chemical Formula I or II as an effective component and a method of using the composition are provided:

[Chemical Formula I]

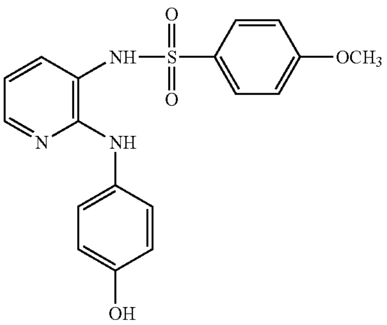

[Chemical Formula II]

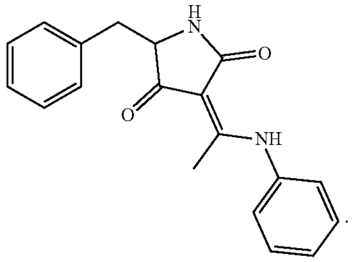

In still another general aspect, a quasi-drug composition for skin moisturizing including a compound represented by the following Chemical Formula I or II as an effective component and a method of using the composition are provided:

[Chemical Formula I]

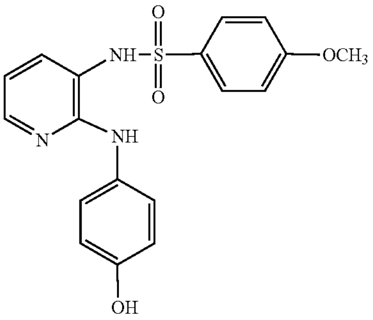

-continued

[Chemical Formula II]

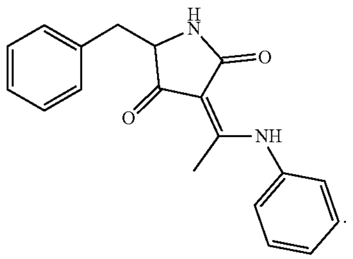

DETAILED DESCRIPTION OF EMBODIMENTS

Figure 1A:
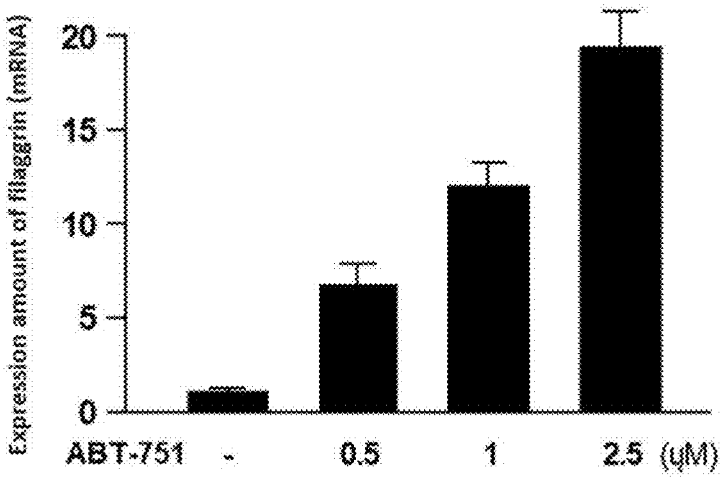
FIGS. 1A and 1B show an increase in an expression amount of filaggrin by treatments with ABT-751 and TN-16, respectively.

Hereinafter, the present invention will be described in detail with reference to accompanying table or drawings.

When a drawing is illustrated, the drawing is provided by way of example so that the idea of the present invention may be sufficiently conveyed to a person skilled in the art. Therefore, the present invention is not limited to the provided drawings, but may be embodied in many different forms, and the drawings may be exaggerated in order to clear the spirit of the present invention.

Herein, technical terms and scientific terms used herein have the general meaning understood by those skilled in the art to which the present invention pertains unless otherwise defined, and a description for the known function and configuration which may unnecessarily obscure the gist of the present invention will be omitted in the following description and the accompanying drawings.

In addition, the singular form used in the specification of the present invention may be intended to also include a plural form, unless otherwise indicated in the context.

In addition, units used in the specification of the present invention without particular mention are based on weights, and as an example, a unit of % or ratio refers to a wt % or a weight ratio.

In addition, in the specification of the present invention, the expression, "comprise" is an open-ended description having a meaning equivalent to the expression such as "provided", "contain", "have", or "is/are characterized", and does not exclude elements, materials or processes which are not further listed. In addition, the expression, "substantially consisting of . . . " means that other elements, materials, or processes which are not listed together with specified elements, materials, or processes may be present in an amount which does not have an unacceptable significant influence on at least one basic and novel technical idea of the invention. In addition, the expression, "consisting of" means that only the described elements, materials, or processes are present.

The term "component", "composition", "composition of a compound", "compound", "drug", "pharmaceutical activator", "activator", "cure", "therapeutic method", "treatment", or "medicine" used in the specification of the present invention is interchangeably used for meaning a compound or a composition of a compound(s) or a material inducing a desired pharmaceutical and/or physiological effect by a topical and/or systemic action when administered to a subject (human or animal).

The term "treatment" or "therapeutic method" (as well as different forms thereof) used in the specification of the present invention includes preventive (e.g., preventive treatment), curative, or mitigating treatment. The term "treating" used in the present application includes alleviating or decreasing at least one harmful or negative effect or symptom of states, diseases, or disorders. The terms "prevention", "improvement", and "treatment" of the present invention should be interpreted in the broadest concept, and "preventing" means preventing one or more of clinical symptoms of a diseases of a patient from progressing, the patient being exposed to or susceptible to the disease but not experiencing or revealing the symptoms of the disease yet. "Treatment" refers to all actions to inhibit or decrease development of a disease or one or more clinical symptoms thereof.

In the present invention, "sample" or "specimen" represents a subject to be analyzed, and is used in the same sense throughout the specification.

The present invention provides a pharmaceutical composition for preventing or treating allergic skin diseases or pruritus cutaneous including a compound represented by the following Chemical Formula I or II or a pharmaceutically acceptable salt thereof as an effective component:

[Chemical Formula I]

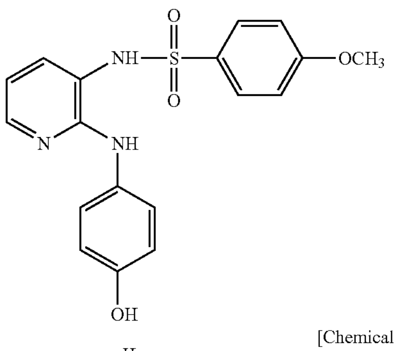

[Chemical Formula II]

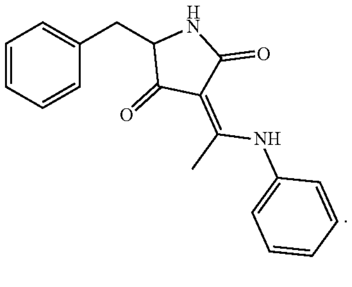

The compound of Chemical Formula I is a compound of CAS registry No. 141430-65-1, which is ABT-751 (N-[2-[(4-Hydroxyphenyl)amino]pyridin-3-yl]-4-methoxybenzenesulfonamide).

ABT-751 is an anticancer agent developed for oral use and an anti-mitotic drug including sulfonamide. Since it shows antitumor activity against extensive tumor cells, it was developed as a therapeutic agent for breast cancer, non-small lung cancer, and the like, but the development was discontinued after that.

The compound of Chemical Formula II is a compound of CAS registry No. 33016-12-5, which is TN-16 (3-[1-(phenylamino)ethylidene]-5-(phenylmethyl)-2,4-pyrrolidinedione).

TN-16 is a new microtubule inhibitor having an antitumor activity, and was synthesized by modifying tenuazonic acid (3-acetyl-5-sec-butyltetramic acid) which is a natural antibiotic separated from a *Alternaria tenuis* culture and characterized. It was found in 1967 that TN-16 has powerful anti-cancer efficacy, but a more powerful drug has not been found in follow-up studies. In addition, it was revealed in 1983 that the action mechanism of TN-16 is to inhibit microtubule formation, and TN-16 acts by binding to a sensitive area. The structure of TN-16 is similar to cytochalasin B which is a standard actin polymerization inhibitor, and it is known that cell cycle arrest is derived in an M group and cytotoxicity of T lymphocytes and natural killer cells is suppressed.

In the present invention, a pharmaceutically acceptable salt refers to a commonly used salt in the pharmaceutical industry, and, as an example, includes an inorganic ion salt prepared with calcium, potassium, sodium, magnesium, and the like, an inorganic acid salt prepared with hydrochloric acid, nitric acid, phosphoric acid, bromic acid, iodic acid, perchloric acid, sulfuric acid, and the like, an organic acid salt prepared with acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like, a sulfonic acid salt prepared with methane sulfonic acid, ethane sulfonic acid, benzene sulfonic acid, p-toluene sulfonic acid, naphthalene sulfonic acid, and the like, an amino acid salt prepared with glycine, arginine, lysine, and the like, an amine salt prepared with trimethylamine, triethylamine, ammonia, pyridine, picoline, and the like, but is not limited thereto.

According to the results of an exemplary embodiment of the present invention, the pharmaceutical composition shows an excellent effect in prevention and treatment of allergic skin diseases, pruritus cutaneous, or both of them, through operation effects, such as enhancing an expression amount of filaggrin which is highly related to the onset of allergic skin diseases, enhancing a skin moisturizing effect to improve a skin barrier function, and also adjusting an inflammatory response of the allergic skin diseases and decreasing skin itchiness.

The allergic skin disease refers to a pathological symptom caused by an allergic reaction mediated by mast cell activation such as mast cell degranulation, and the allergic skin disease includes, representatively, atopic dermatitis, allergic dermatitis, contact dermatitis, and the like.

Pruritus cutaneous is a disease including pruritus caused by decreased antibacterial activity and deteriorated barrier function due to a decrease of a lipid content in the cornified layer of skin or pruritus caused by external stimulation such as a temperature change, chemicals, and electrical stimulation.

The term “anti-allergic” in the present invention is used in the sense including improvement (alleviation of symptoms), treatment, and prevention (inhibition or delay of onset) of an allergic skin disease.

The allergic skin disease may be, as an example, atopic dermatitis, and the atopic dermatitis shows symptoms such as dry eczema skin or papule, and epidermal hyperplasia, cuticularization, and accumulation of lymphocytes and mast cells, and the like are confirmed in lesion samples of atopic patients. Atopic dermatitis patients may suffer from severe pruritus cutaneous, which causes inflammation of skin lesions to further worsen clinical symptoms.

Skin is anatomically positioned in the outermost of a body, and blocks the direct entry of pathogenic microorganisms, viruses, chemicals, and the like in the air into the body, thereby performing an important barrier function to protect the body from the external environment and prevent excessive leakage of body moisture. A skin tissue has a layered structure of a basal layer, a spinous and granular layer, and a cornified layer, and a particular expression marker in each layer structure is well known. Among them, keratin 1 (K1) and keratin 10 (K10) are expressed in the spinous and granular layer and filaggrin is expressed in the top/epithelium including a cornified layer, and these are one of the main proteins which are essential for forming a barrier function specific to the skin described above.

Recently, a correlation between atopic dermatitis and filaggrin gene abnormality was revealed from the atopic dermatitis patients as described above, and in particular, in Europe, filaggrin gene mutation was detected in more than a half of the total number of atopic patients. Also, it was revealed in Japan that about 25% of atopic patients had filaggrin gene mutation, and in various Asian countries including China and Korea also, filaggrin gene mutation was detected in patients with dermatitis including atopic dermatitis.

It has been reported that the filaggrin gene abnormality causes decreased filaggrin protein expressed in skin and a loss of a skin barrier function, and promotes penetration of an antigen such as an allergic stimulator to cause dermatitis. Actually, among atopic patients, patients having filaggrin abnormality easily progress to allergic diseases such as asthma and rhinitis, and a diagnosis method for determining whether there is filaggrin gene abnormality and development of a therapeutic agent are needed.

The atopic dermatitis may be caused by reduced expression of filaggrin, and when the reduced expression of filaggrin is 5.0% or more as compared with a normal person, the pharmaceutical composition may be administered to a patient.

In a specific exemplary embodiment of the present invention, the compound represented by Chemical Formula I enhances expression of filaggrin and enhances a skin moisturizing effect, thereby showing an excellent improvement effect in terms of a skin barrier index and a skin composite index. In addition, the compound greatly inhibits an inflammatory response in an allergic skin disease model, inhibits epidermal hyperplasia, cuticularization, and the like, adjusts inflammatory cytokine, and decreases skin itchiness, thereby showing excellent prevention, treatment, and improvement effects for allergic skin diseases and/or pruritus cutaneous. Herein, inflammatory cytokine refers to cytokine which causes an inflammatory response occurring in the body, and is used in an ordinary sense in the art to which the present invention pertains. For example, IL-2, IL-4, IL-13, and the like may act as an inflammatory cytokine to cause an allergic skin disease.

As an example, when a person has filaggrin expression decreased by 5.0% or more, preferably 5.3% or more, and more preferably 5.6% or more as compared with a normal person, he/she may be determined to be a patient suffering from atopic dermatitis, and thus, the pharmaceutical composition according to the present invention may be administered to the patient for treating the atopic dermatitis.

The pharmaceutical composition may further include appropriate carriers, excipients, and diluents which are commonly used in pharmaceutical compositions, in addition to the compound represented by Chemical Formula I or the pharmaceutically acceptable salt thereof.

The carriers, excipients, and diluents which may be included in the composition may include, unlimitedly, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, and the like. When the composition is formulated, it may be formulated using commonly used diluents or excipients such as fillers, extenders, binders, wetting agents, disintegrants, and surfactants.

The pharmaceutical composition may be formulated in various forms according to a common method, and when it is formulated into a transdermal administration agent, an ointment agent, a cream agent, a lotion agent, a gel agent, an external solution agent, a paste agent, a liniment agent, an airol agent, and the like are preferred as an appropriate formulation, but the composition is not limited thereto.

The pharmaceutical composition according to the present invention may further include preservatives, stabilizers, wetting agents, emulsifiers, solubilizers, sweeteners, colorants, osmotic pressure regulators, antioxidants, and the like, in addition to the above carriers.

The formulation of the pharmaceutical composition is known in the art, and specifically, documents such as Remington's Pharmaceutical Sciences (19th ed., 1995) may be referred. The above document is regarded as a part of the present specification.

The pharmaceutical composition according to the present invention may be administered in a pharmaceutically effective amount.

In the present invention, an “pharmaceutically effective amount” refers to an amount sufficient to treat a disease at a reasonable benefit/risk ratio applicable to medical treatment, and an effective dose level may be determined by factors including the kind and severity of the disease of a patient, an activity of a drug, sensitivity to a drug, administration time, administration route and releasing rate, treatment period, and a simultaneously used drug, and other factors well known in the medical field. The pharmaceutical composition according to the present invention may be administered as an individual therapeutic agent or in combination with other therapeutic agents, may be administered sequentially or simultaneously with a conventional therapeutic agent, and may be administered in a single or multiple dose. Taking the factors into account, it is important to administer the composition in a minimum amount to obtain a maximum effect without any side effect, and this will be easily determined by a person skilled in the art.

The pharmaceutical composition of the present invention may be administered to an individual through various routes. An administration manner may be through various oral and parenteral formulations, and when the composition is formulated, it may be formulated using a commonly used excipient, and preferably, may be used as a liniment for skin application as a parenteral drug in the present invention. The administration mode of the pharmaceutical composition of the present invention is determined depending on the type of drug as an active component, together with various related factors such as diseases to be treated, administration routes, a patient's age, gender, and weight, and disease severity.

In addition, the present invention provides a cosmetic composition for preventing or improving allergic skin diseases or pruritus cutaneous including a compound represented by the following Chemical Formula I or II or a pharmaceutically acceptable salt thereof as an effective component:

[Chemical Formula I]

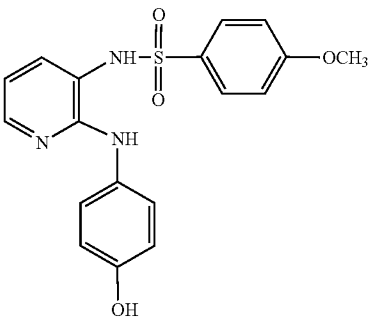

[Chemical Formula II]

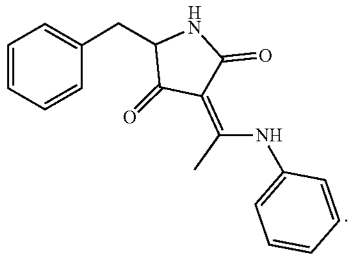

The cosmetic composition may be any one formulation selected from the group consisting of a solution, an external ointment, a cream, a foam, a nourishing lotion, a softening lotion, a pack, a softener, a milky lotion, a makeup base, an essence, a soap, a liquid detergent, a bath preparation, a sunscreen cream, a sun oil, a suspension, an emulsion, a paste, a gel, a lotion, a powder, a soap, a surfactant-containing cleanser, an oil, a powder foundation, an emulsion foundation, a wax foundation, a patch, and a spray, but is not limited thereto.

In addition, the cosmetic composition of the present invention may further include one or more cosmetically acceptable carriers blended with common skin cosmetics, and as a usual component, for example, oil, water, surfactant, moisturizer, lower alcohol, thickener, chelating agent, colorant, preservative, fragrance, and the like may be properly blended, but the composition is not limited thereto.

A cosmetically acceptable carrier included in the cosmetic composition of the present invention is various depending on the formulation.

When the formulation of the present invention is an ointment, a paste, a cream, or a gel, animal oil, vegetable oil, wax, paraffin, starch, tragacanth, cellulose derivatives, polyethylene glycol, silicone, bentonite, silica, talc, zinc oxide, or a mixture thereof as a carrier component may be used.

When the formulation of the present invention is a powder or a spray, lactose, talc, silica, aluminum hydroxide, calcium silicate, polyamide powder, or a mixture thereof may be used as a carrier component, and in particular, when the formulation is a spray, a propellant such as chlorofluorohydrocarbon, propane/butane, or dimethyl ether may be further included.

When the formulation of the present invention is a solution or an emulsion, a solvent, a solubilizer, or an emulsifier is used, for example, water, ethanol, isopropanol, ethyl carbonate, ethyl acetate, benzyl alcohol, benzyl benzoate, propylene glycol, and 1,3-butylglycol oil may be used, and in particular, cottonseed oil, peanut oil, corn germ oil, olive oil, castor oil, and sesame oil, glycerol aliphatic ester, polyethylene glycol, or fatty acid ester of sorbitan may be used, as a carrier component.

When the formulation of the present invention is suspension, a liquid diluent such as water, ethanol, or propylene glycol, a suspension such as ethoxylated isostearyl alcohol, polyoxyethylene sorbitol ester, and polyoxyethylene sorbitan ester, microcrystalline cellulose, aluminum metahydroxide, bentonite, agar, or tragacanth, and the like may be used as a carrier component.

When the formulation of the present invention is a soap, an alkali metal salt of a fatty acid, a fatty acid hemiester salt, a fatty acid protein hydrolysate, isethionate, lanoline derivatives, aliphatic alcohol, vegetable oil, glycerol, sugar, and the like may be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oil, lanoline derivatives, or ethoxylated glycerol fatty acid ester, and the like may be used as a carrier component.

The cosmetic composition according to the present invention may include 0.01 to 20 wt % of the compound of Chemical Formula I or II with respect to the total weight of the composition.

In addition, the present invention provides a cosmetic composition for skin moisturizing including a compound represented by the following Chemical Formula I or II or a pharmaceutically acceptable salt thereof as an effective component:

[Chemical Formula I]

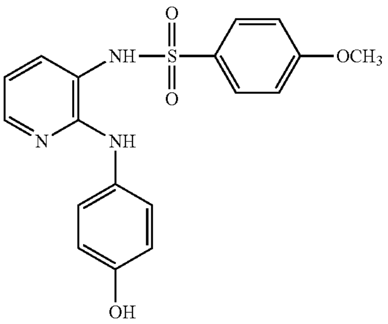

-continued

[Chemical Formula II]

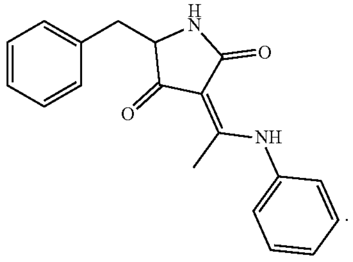

The skin moisturizing may refer to increasing moisture in the skin and maintaining a moist state, and the cosmetic composition for skin moisturizing according to the present invention has an excellent skin moisturizing effect of suppressing or decreasing skin moisture loss, and adjusts expression of factors such filaggrin, involucrin, and loricrin which are moisturizing-related factors, thereby showing an excellent effect on skin moisturizing.

In addition, the present invention provides a quasi-drug composition for skin moisturizing including the compound represented by the following Chemical Formula I or II or a pharmaceutically acceptable salt thereof as an effective component:

[Chemical Formula I]

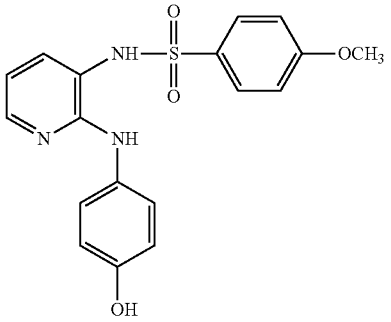

[Chemical Formula II]

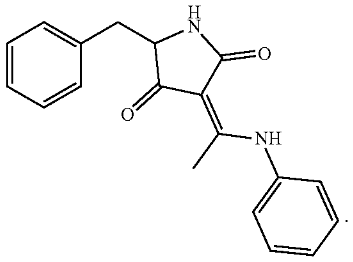

The quasi-drug composition is a quasi-drug composition for skin moisturizing.

The quasi-drug refers to an article having less effective than a medicine, among articles used for diagnosing, treating, improving, alleviating, curing, or preventing diseases in humans or animals, and for example, according to the pharmaceutical affairs act, the quasi-drug includes fiber/rubber products used for treating or preventing diseases in humans/animals, a non-appliance, a non-machinery, or similar articles which have insignificant influences on or do not directly act upon human bodies, fungicides/pesticides for preventing infectious diseases, and the like, excluding articles used for a medicine, but is not limited thereto.

The kind or formulation of quasi-drug composition of the present invention is not particularly limited, but preferably, may be a disinfectant cleanser, a shower foam, a mouthwash, a wet wipe, a detergent soap, a hand wash, a humidifier filler, a mask, an ointment agent, a filter filler, or the like.

When the composition of the present invention is included in the quasi-drug for skin moisturizing, the composition may be included as it is or used with other quasi-drug components, and may be properly used according to a usual method. A mixing amount of the effective component may be appropriately determined depending on the purpose of use, and the quasi-drug composition according to the present invention may include 0.01 to 20 wt % of the compound of Chemical Formula I or II with respect to the total weight of the composition.

In addition, the present invention provides a method of treating allergic skin diseases or pruritus cutaneous including administering a pharmaceutical composition including the compound represented by the following Chemical Formula I or II or a pharmaceutically acceptable salt thereof to a patient:

[Chemical Formula I]

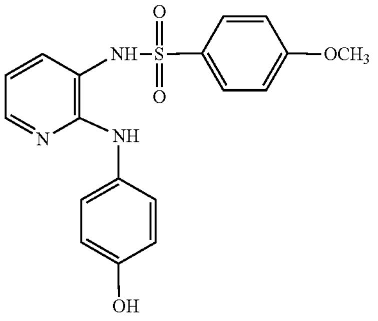

[Chemical Formula II]

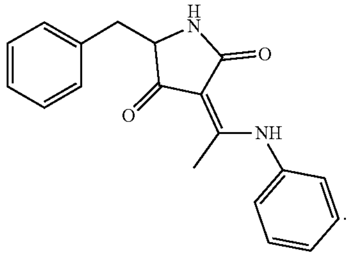

The treatment method may include, as an example, administering the pharmaceutical composition to a patient by a) measuring an expression amount of filaggrin of a patient; and b) when the expression amount of filaggrin is decreased by 5.0% or more as compared with a normal person, determining whether administration of the pharmaceutical composition is required for the patient, but is not limited thereto, and the amount and the administration cycle of the pharmaceutical composition administered to the patient may vary depending on the amount of filaggrin decreased, and as an example according to an exemplary embodiment of the present invention, the pharmaceutical composition may be administered once a day for 1 to 4 weeks at a concentration of 0.5-2.5 μM, but the present invention is not limited thereto.

Hereinafter, the present invention will be described in more detail by the following examples. These examples are provided only for illustrating the present invention, and it will be apparent to a person skilled in the art that the scope of the present invention is not construed as being limited by the examples.

[Materials, Reagents, Strains, Devices, and the Like]

A human epidermal cell line (normal human epidermal keratinocyte; NHEK) is a human fetal transdermal cell line and was used after being distributed from ATCC.

It was a cell obtained from primary culture and was used for confirming biochemical changes within the cell by ABT-751 or TN-16 under normal conditions, not disease conditions.

Experimental animal: Since a hos:HR-1(hairless) mouse has no hair in skin disease research, it allows skin-related research to be performed by directly applying a drug on skin or inducing skin diseases by chemical or biological allergen.

In addition, it has a skin thickness of about 0.4 mm at 8 to 10 weeks of age, which is similar to the skin of a human, and is useful for research on pathogenesis mechanism of skin diseases and confirmation of biochemical changes in skin tissue.

Test Example 1

1.1 Measurement of Expression Amount of Filaggrin Using RNA Extraction and RT-qPCR A normal human epidermal keratinocyte (NHEK) on which ABT-751, TN-16, or a control sample was applied, or a mouse skin tissue was dissolved using a TRI reagent (MRC), and then RNA in cells was extracted using Rneasy Mini Kit (Qiagen).

The extracted RNA was reverse-transcribed with ImProm-II TM Reverse Transcription Kit (Promega) to synthesize cDNA, and then an amount of filaggrin was measured by a quantitative PCR (qPCR) through Real-Time PCR Detection System (Bio-Rad, CFX96).

1-2. Protein Extraction and Western Blot

A part of the collected tissue was homogenized using a tissue homogenizer (Daihan Scientific), dissolved using a cell lysis buffer (RIPA buffer, Invitrogen), and centrifuged with a centrifuge, and a supernatant was transferred to a new tube and used as a protein sample.

30 μg of a protein sample was loaded onto a PAGE gel (Invitrogen) having a concentration gradient of 4% to 12%, and SDS-PAGE using a Running buffer (Invitrogen) and an electrophoresis machine (Bio-Rad) was performed to separate protein by molecular weight.

The separated protein was transferred to a PVDF thin film (Bio-Rad), and then blocked with a 5% blocking solution (Skim milk; BD).

The thin film was reacted with a filaggrin antibody (Santa Cruz) or a GAPDF antibody (Abcam) for 16 hours, washed, reacted again with a second antibody for 1 hour, and washed.

The thin film was reacted with an ECL solution (Thermo Fisher), and the protein after the reaction was detected using a luminescence reaction measuring instrument (Fusion Solo, Vilber).

[Test Example 2] Skin Barrier Function Test 2 hours after applying ABT-751 or TN-16, skin moisture loss, a skin barrier index, and a comprehensive index on the application area were measured for 3 weeks with a precision measuring instrument (Courage-khazaka electronic GmbH, MPA10), and recorded.

[Example 1] Expression Amount of Filaggrin and Cell Differentiation Degree in Normal Human Epidermal Keratinocytes by Treatment with ABT-751 or TN-16

The normal human epidermal keratinocytes (NHEK) in culture was treated with ABT-751 and TN-16, respectively to measure the expression amount of filaggrin and confirm a change in cell differentiation degree.

NHEK was treated with ABT-751 and TN-16 by concentrations of 0, 0.5, 1.0, and 2.5 μM, respectively, and after 24 hours of treatment, the expression amount of filaggrin and the cell differentiation degree were observed.

Figure 1B:
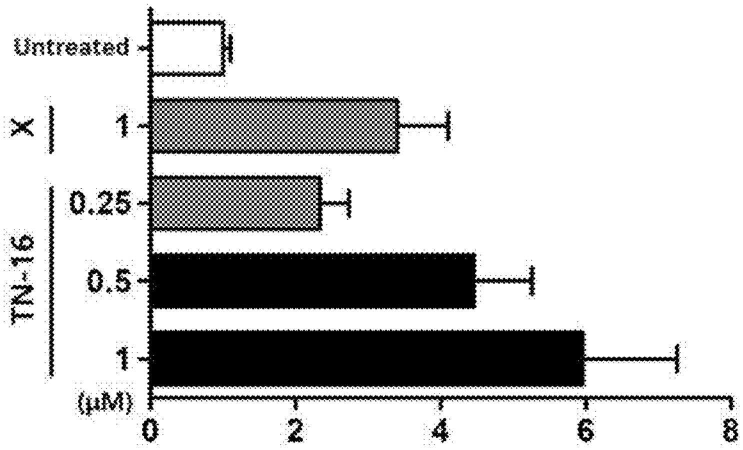
Figure 2:
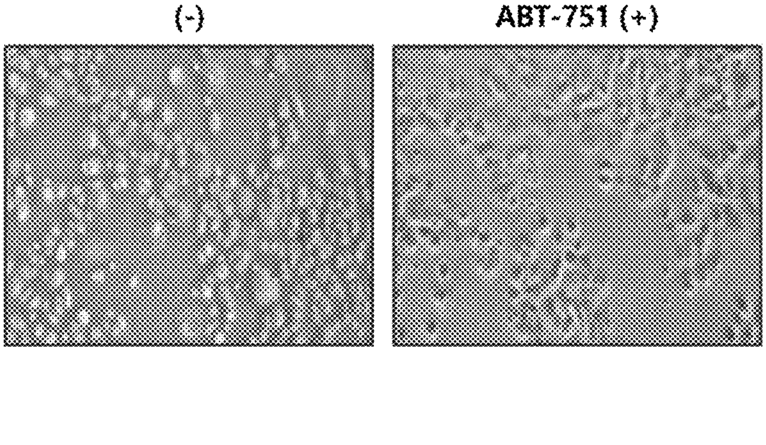
FIG. 2 shows an increase in a cell differentiation degree by a treatment with ABT-751.

The results are shown in FIGS. 1 and 2.

It was confirmed therefrom that the expression amount of filaggrin increased depending on the ABT-751 and TN-16 treatment concentrations (see FIGS. 1A and 1B), and the cell differentiation degree was significantly increased in the ABT-751-treated group as compared with ABT-751-untreated group (control group) (see FIG. 2).

[Example 2] Expression Amount of Filaggrin and Cell Differentiation Degree in Animal Cells by Treatment with ABT-751 or TN-16

ABT-751 and TN-16 of 0, 1, 2, and 4% formulations were applied on the back skin of a hairless hos:HR-1 mouse (hereinafter, referred to as HR-1 mouse) in the same amount once a day for 3 weeks, respectively.

After each application, skin moisture loss and a skin barrier index were measured by the method of the test example.

After application for 2 weeks, the HR-1 mouse was euthanized in a carbon dioxide chamber, and back skin tissues were collected, respectively.

2-1. Measurement of Expression Amount of Filaggrin

Each of RNA and protein was extracted from the back skin tissue on which ABT-751 or TN-16 was applied, respectively, by the method of the text example and the expression amount of filaggrin was measured, and the results are shown in FIG. 3.

Figure 3A:
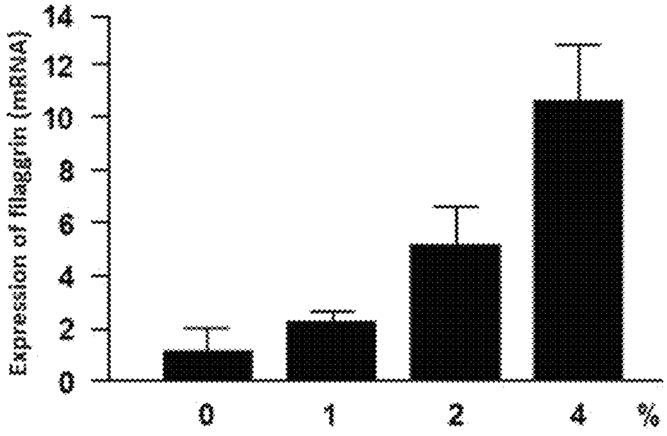
FIGS. 3A to 3C show an increase in an expression amount of filaggrin in HR-1 mouse skin by treatments with ABT-751 (3A and 3C) and TN-16 (3C), respectively.
Figure 3B:
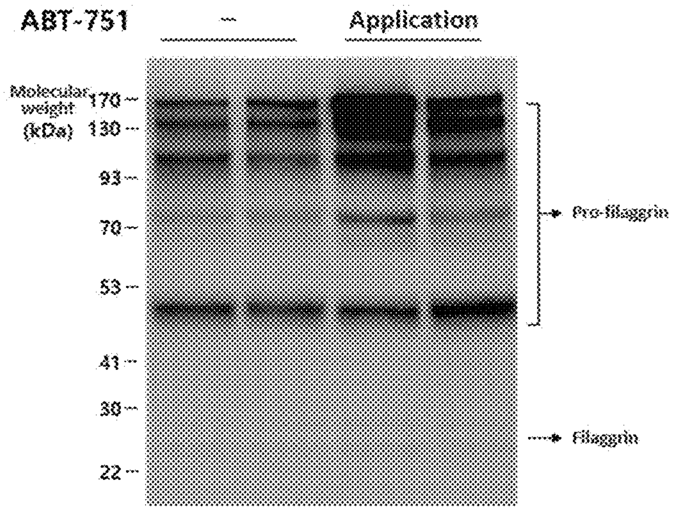
Figure 3C:
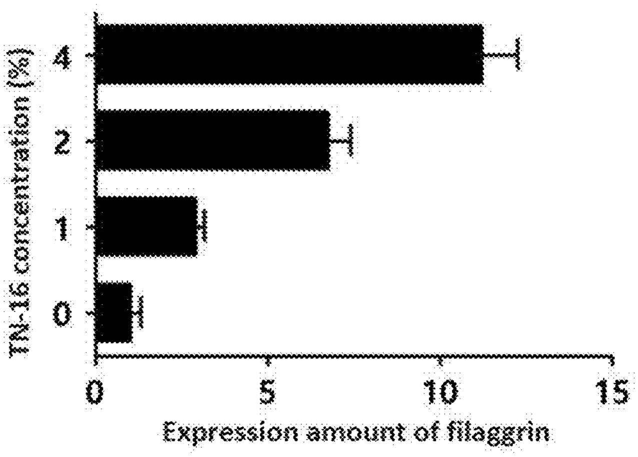
Figure 4A:
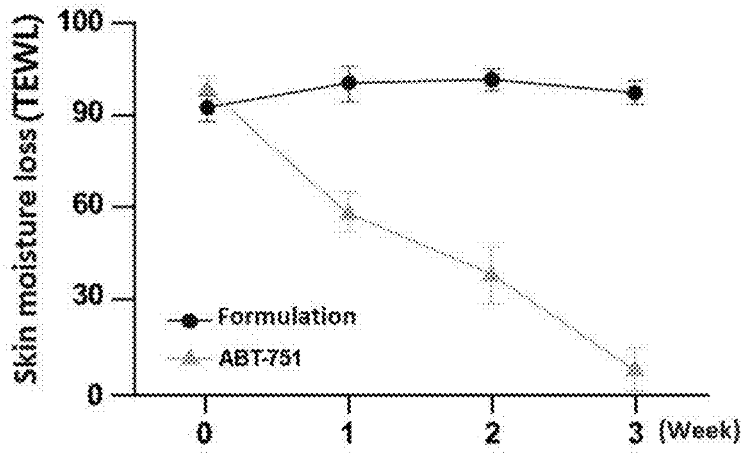
FIGS. 4A to 4D show a decrease in skin moisture loss and an increase in skin barrier index of a HR-1 mouse by applications of ABT-751 (4A and 4B) and TN-16 (4C and 4D) in 4% formulations, respectively.
Figure 4B:
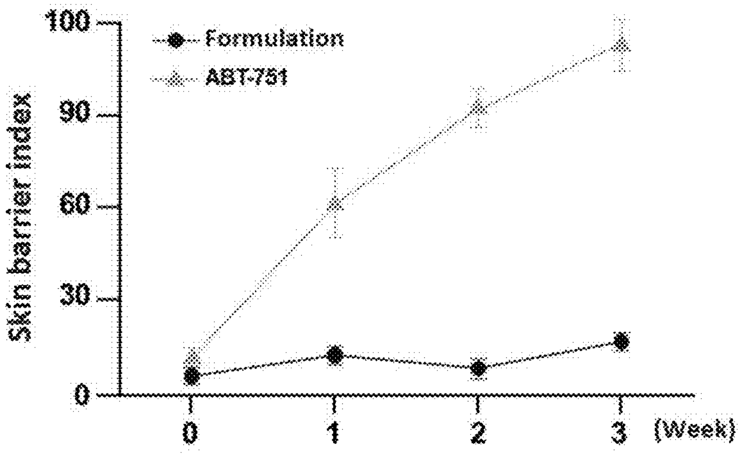
Figure 4C:
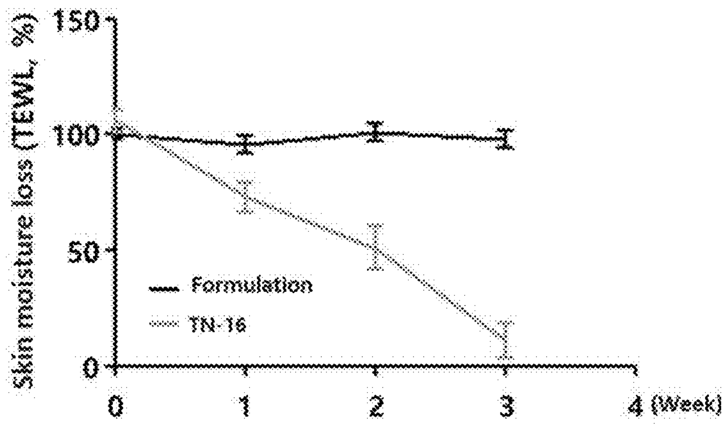
Figure 4D:
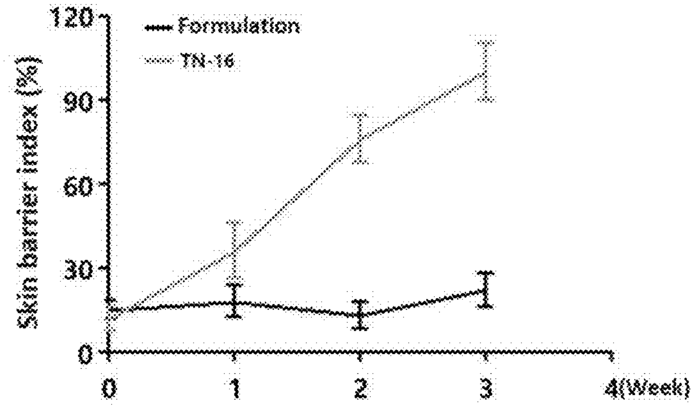

It was confirmed therefrom that the expression amount of filaggrin in the skin tissue increased in a concentration-dependent manner, after applying ABT-751 or TN-16 of the remaining formulations, as compared with the control group (0% formulation ABT-751 or 0% formulation TN-16) (see FIGS. 3A to 3C).

2-2. Measurement of Skin Moisture Loss and Skin Barrier Index

After applying the control group (0% formulation ABT-751 or 0% formulation TN-16) and ABT-751 or TN-16 of a 4% formulation, respectively, skin moisture loss and a skin barrier index were measured, and the results are shown in FIG. 4.

It was confirmed therefrom that the skin moisture loss in the area applied in the HR-1 mouse decreased and the skin barrier index increased by applying ABT-751 or TN-16 of a 4% formulation (see FIGS. 4A to 4D).

In particular, as the number of days of application passed, it was confirmed that a decrease in the skin moisture loss and an increase in the skin barrier index increased.

The composition for preventing, improving, or treating atopic dermatitis according to the present invention was confirmed to effectively increase filaggrin expression in skin cells and improve a skin barrier function, thereby showing an effect of effectively improving or treating symptoms of pruritus cutaneous or allergic skin diseases including atopic dermatitis, and thus, showing an excellent skin moisturizing effect.

Hereinabove, the specific parts of the present invention have been described in detail, and it will be apparent that the specific description as such is only a preferred embodiment to a person skilled in the art and the scope of the present invention is not limited thereby. Thus, the substantial scope of the present invention will be defined by the appended claims and their equivalents.

What is claimed is:

1. A method of treating allergic skin diseases or pruritus cutaneous, the method comprising: administering an effective amount of a pharmaceutical composition including a compound represented by the following Chemical Formula I or II or a pharmaceutically acceptable salt thereof as an effective component:

[Chemical Formula I]

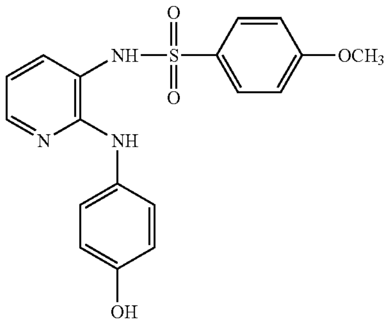

[Chemical Formula II]

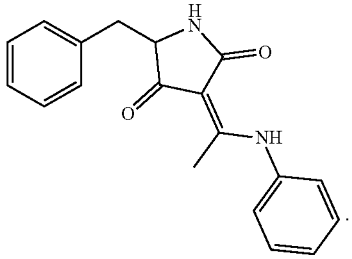

2. The method of treating allergic skin diseases or pruritus cutaneous of claim 1, wherein the allergic skin disease is atopic dermatitis or contact dermatitis.

3. The method of treating allergic skin diseases or pruritus cutaneous of claim 1, wherein the allergic skin disease is atopic dermatitis.

4. The method of treating allergic skin diseases or pruritus cutaneous of claim 1, wherein the pharmaceutical composition is administered by skin application.

5. The method of treating allergic skin diseases or pruritus cutaneous of claim 1, wherein the atopic dermatitis is caused by reduced expression of filaggrin.

6. The method of treating allergic skin diseases or pruritus cutaneous of claim 5, wherein when the reduced expression of filaggrin is 5.0% or more as compared with a normal person, the pharmaceutical composition is administered to a patient.

7. The method of treating allergic skin diseases or pruritus cutaneous of claim 1, wherein the pharmaceutical composition is any one formulation selected from the group consisting of an ointment agent, a cream agent, a lotion agent, a gel agent, an external solution agent, a paste agent, a liniment agent, and an airol agent.

8. A method of improving allergic skin diseases or pruritus cutaneous, the method comprising: administering an effective amount of a cosmetic composition including a compound represented by the following Chemical Formula I or II or a pharmaceutically acceptable salt thereof as an effective component:

[Chemical Formula I]

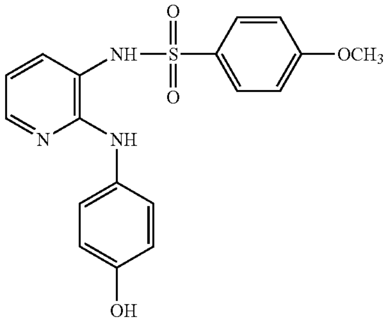

[Chemical Formula II]

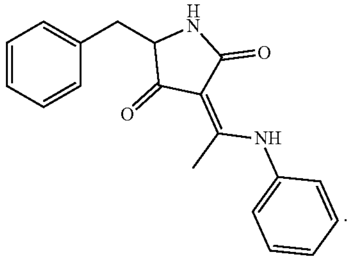

9. The method of improving allergic skin diseases or pruritus cutaneous of claim 8, wherein the cosmetic composition is any one formulation selected from the group consisting of a solution, an external ointment, a cream, a foam, a nourishing lotion, a softening lotion, a pack, a softener, a milky lotion, a makeup base, an essence, a soap, a liquid detergent, a bath preparation, a sunscreen cream, a sun oil, a suspension, an emulsion, a paste, a gel, a lotion, a powder, a soap, a surfactant-containing cleansing, an oil, a powder foundation, an emulsion foundation, a wax foundation, a patch, and a spray.

10. A method of skin moisturizing, the method comprising: administering an effective amount of a cosmetic composition including a compound represented by the following Chemical Formula I or II or a pharmaceutically acceptable salt thereof as an effective component:

[Chemical Formula I]

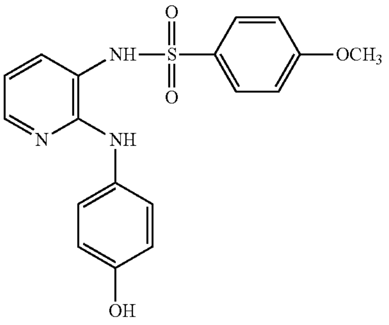

[Chemical Formula II]

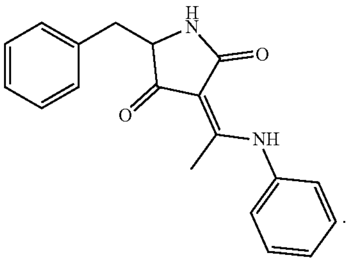

11. A method of skin moisturizing, comprising administering an effective amount of a quasi-drug composition including a compound represented by the following Chemical Formula I or II or a pharmaceutically acceptable salt thereof as an effective component:

[Chemical Formula I]

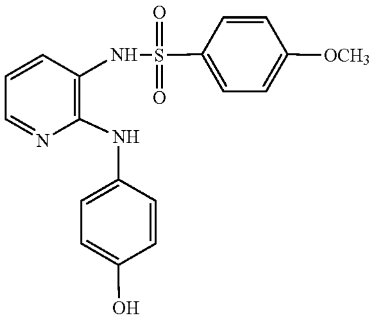

[Chemical Formula II]

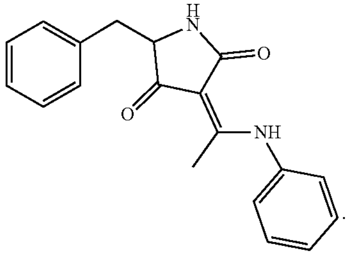

12. The method of treating allergic skin diseases or pruritus cutaneous of claim 1, wherein the administrating is performed orally or parenterally.

* * * * *